(12) United States Patent
Abbyad et al.

(10) Patent No.: US 9,512,466 B2
(45) Date of Patent: Dec. 6, 2016

(54) MICRODROPLET FORMATION BY WELLS IN A MICROFLUIDIC DEVICE

(71) Applicant: Santa Clara University, Santa Clara, CA (US)

(72) Inventors: Paul Abbyad, Santa Clara, CA (US); Jonathan Tullis, Santa Clara, CA (US); Cedar A. Waldherr Smith, Santa Clara, CA (US)

(73) Assignee: Santa Clara University, Santa Clara, CA (US)

( * ) Notice: Subject to any disclaimer, the term of this patent is extended or adjusted under 35 U.S.C. 154(b) by 72 days.

(21) Appl. No.: 14/660,304

(22) Filed: Mar. 17, 2015

(65) Prior Publication Data

US 2015/0267247 A1    Sep. 24, 2015

Related U.S. Application Data

(60) Provisional application No. 61/968,556, filed on Mar. 21, 2014.

(51) Int. Cl.
| | |
|---|---|
| *B81B 7/04* | (2006.01) |
| *B01J 13/02* | (2006.01) |
| *B01J 14/00* | (2006.01) |
| *C12Q 1/68* | (2006.01) |
| *B01J 19/00* | (2006.01) |
| *B01J 13/16* | (2006.01) |

(52) U.S. Cl.
CPC .......... *C12Q 1/6806* (2013.01); *B01J 19/0046* (2013.01); *B01J 13/16* (2013.01); *B01J 2219/00596* (2013.01); *B01J 2219/00734* (2013.01); *Y10T 137/0391* (2015.04)

(58) Field of Classification Search
CPC ................. B01J 3/502784; B01J 2200/0673; B01J 13/02; Y10T 436/2575
See application file for complete search history.

(56) References Cited

U.S. PATENT DOCUMENTS

2010/0252118 A1* 10/2010 Fraden .............. B01L 3/502746
137/2

OTHER PUBLICATIONS

Tomasi et al., "High Density Hydrogel Arrays for 3D Cell Colonies With Dynamically Controlled External Stimuli" 17th International Conference on Miniaturized Systems for Chemistry and Life Sciences Oct. 27-31, 2013,Freiburg Germany.

* cited by examiner

*Primary Examiner* — Paul Hyun
(74) *Attorney, Agent, or Firm* — Lumen Patent Firm

(57) ABSTRACT

A method of forming microdroplets is provided that includes forming a well plate, using lithography, where the well plate includes a microchannel and a microwell in a surface of the fluid channel, flowing a first fluid into the microchannel, where the microchannel and the microwell are filled with the first fluid, and flowing a second fluid into the microchannel, where the first fluid is displaced from the microchannel, where the first fluid remains in the microwell, where a microdroplet of the first fluid is formed.

20 Claims, 2 Drawing Sheets

MICRODROPLET FORMATION BY WELLS IN A MICROFLUIDIC DEVICE

CROSS-REFERENCE TO RELATED APPLICATIONS

This application claims priority from U.S. Provisional Patent Application 61/968,556 filed Mar. 21, 2014, which is incorporated herein by reference.

FIELD OF THE INVENTION

The present invention relates generally to microfluidics. More particularly, the invention relates to a device and method for droplet formation used in microfluidics.

BACKGROUND OF THE INVENTION

Conventional techniques to make microdroplets in series include flowing immiscible liquids through a constriction or in a cross-flow geometry. However with these techniques, size uniformity and stability are problematic, in addition to the positioning of the droplets in preparation for analysis and detection. These methods form the droplets in series, where the time of droplet formation can be an issue.

What is needed is a method of forming uniform and controlled size microdroplets in parallel at precise locations in a microfluidic device.

SUMMARY OF THE INVENTION

To address the needs in the art, a method of forming microdroplets is provided that includes forming a well plate, using lithography, where the well plate includes a microchannel and a microwell in a surface of the microchannel, flowing a first fluid into the microchannel, where the microchannel and the microwell are filled with the first fluid, and flowing a second fluid into the microchannel, where the first fluid is displaced from the microchannel, where the first fluid remains in the microwell, where a microdroplet of the first fluid is formed.

According to one aspect, the invention further includes priming the microchannel, using the second fluid, where the second fluid is flowed into the microchannel to fill the microchannel prior to the flowing the first fluid into the microchannel, where the microwell is coated with a thin film of the second fluid.

In another aspect of the invention, the well can include a shape such as a cylinder, a rectangle, an oval or a hemisphere. In one aspect, the diameter of the micro well is in a range of 0.1 µm to 0.5 cm.

In a further aspect of the invention, the microchannel includes a height in a range of 0.1 µm to 0.1 cm.

According to one embodiment of the invention, the microchannel includes an array of the microwells. Here, an aspect ratio of the diameter of the microwell to a minimum spacing between each of the microwells are in a range of 20:1 to 1:10.

In another aspect of the invention, the microchannel includes a material such as glass, PDMS, plastics or polymers.

In yet another aspect of the invention, the lithography includes soft lithography.

According to another aspect of the invention, the microchannel is treated with a hydrophobic coating, where the microwells comprise the hydrophobic coating.

In a further aspect of the invention, the microchannel is treated with a hydrophilic coating, where the microwells comprise the hydrophilic coating.

In one aspect of the invention, the flow speeds of the fluids in the microchannel are in a range of 0.01 to 500 mm/sec.

In another aspect of the invention, an aspect ratio of a depth of the microchannel to a depth of the microwell is in a range of 1:1.1 to 1:20.

In yet another aspect of the invention, a surfactant is added to the microdroplet or to the first fluid or to the second fluid, where an interfacial tension of the microdroplet is reduced, where surface wetting of the microdroplets is reduced.

According to one aspect of the invention, the microdroplet is ejected from the microchannel using an external fluid at a flow rate greater than 0.1 mm/sec. Here, the external fluid can include FC-40, hexadecane, mineral oil, silicone oil or water.

In another aspect of the invention, the first fluid or the second fluid includes a gelling reagent, where the flowing of the gelling reagent into the microchannel occurs at a liquid temperature for the gelling reagent.

In a further aspect of the invention, the first solution includes a polymer solution, where the polymer solution in the microwell is polymerized using a polymerizer selected from the group consisting of light, temperature and chemical reaction.

According to one aspect of the invention, the droplet includes a lipid-stabilized aqueous microdroplet, where the first fluid includes an aqueous liquid containing a second lipid that is used to interface the lipid-stabilized aqueous microdroplet, where the oil-second lipid interface traverses the microchannel the said lipid-stabilized aqueous microdroplet to form a lipid bilayer on the microdroplet, where the lipid bilayer microdroplet includes an aqueous outer layer to form a giant-unilamellar vesicle. In another aspect, a plurality of liquid entries disposed in the microchannel are used to produce the microdroplets with variable and predictable lipid-stabilized composition and content across an array of said microwells of the microchannel.

In yet another aspect of the invention, an emulsion having variable microdroplet sizes or homogeneous microdroplet sizes is used to create an organized array of said droplets in a well array, wherein said droplets are ejected from said well array by an external fluid.

DETAILED DESCRIPTION

The current invention includes a method of forming uniform and controlled size microdroplets in parallel at precise locations in a microfluidic device by the successive flow of immiscible fluids over microfabricated wells. The current invention solves the problem of how to form and position droplets quickly and efficiently in a 2D array for biological assays and concurrent detection. According to one embodiment, the drops are made in parallel, which increases the speed of droplet production for assays that require a large number of individual droplets.

Figure 1A:
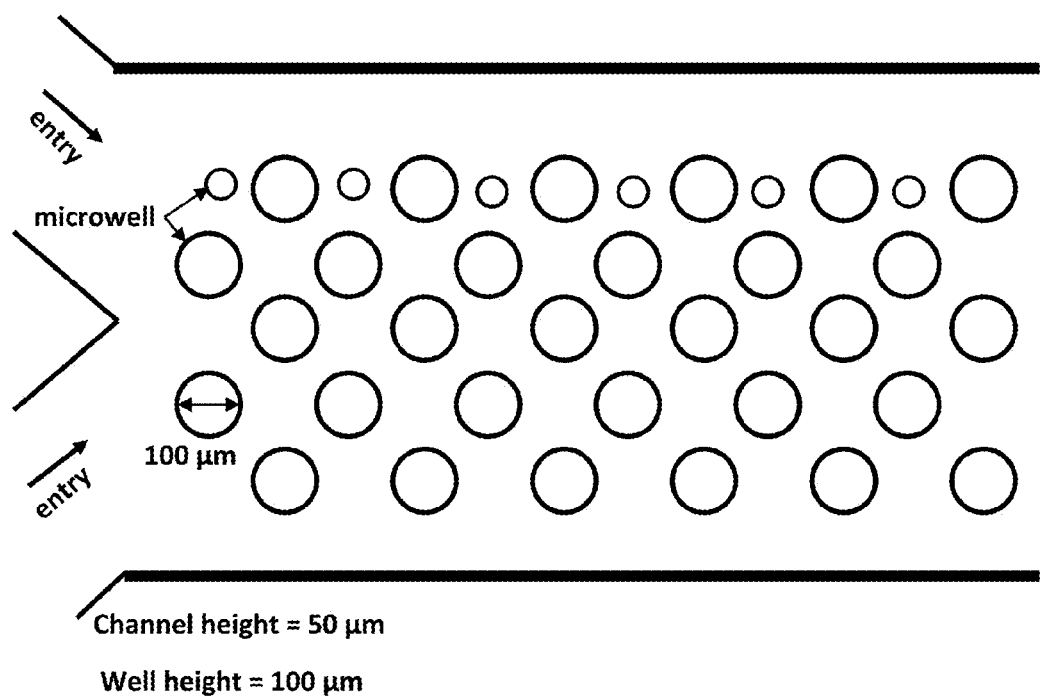
FIGS. 1A-1B show a schematic view of the geometry of a microfluidic channel (FIG. 1A) top view, (FIG. 1B) side view, according to one embodiment of the invention.
Figure 1B:
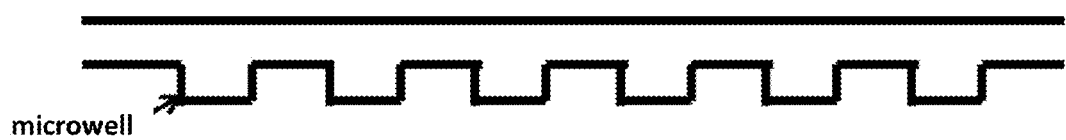

According to one embodiment, a well system is provided to form droplets, where the wells can be cylindrical or hemispherical. The microsystem contains a wide channel of specified height with depressions or wells of greater height. FIG. 1A shows the channel with a height of 50 microns and wells a circular diameter of 100 microns. According to other embodiments of the invention the channel height can be in a range of 0.1 µm to 0.1 cm, the well diameter can be in a range of 0.1 µm to 0.5 cm. FIG. 1B shows a side view one embodiment of the microsystem, where the wells can have a depth in a range of 0.11 µm to 0.1 cm.

Figure 2A:
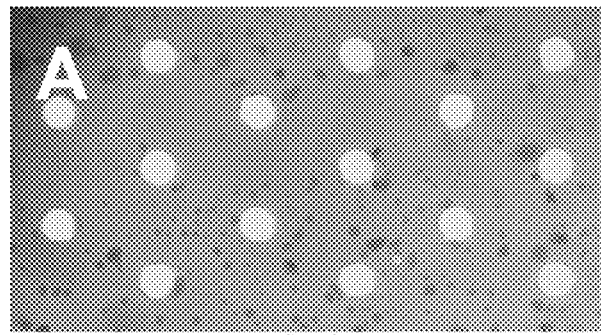
FIGS. 2A-2D show the formation of droplets using wells (FIG. 2A) and the channel is filled with aqueous phase containing fluorescein dye, (FIG. 2B) and (FIG. 2C) oil replaces the aqueous phase producing aqueous droplets in well, and (FIG. 2D) final array of aqueous droplets in wells, according to one embodiment of the invention.
Figure 2B:
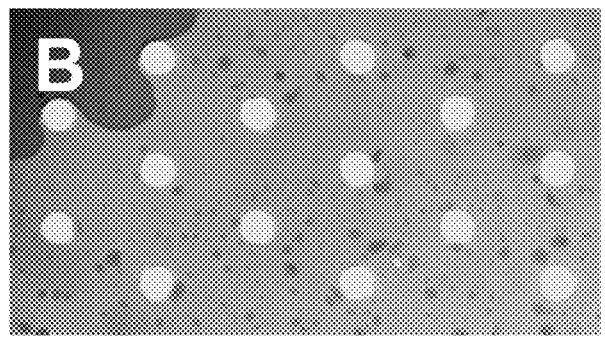
Figure 2C:
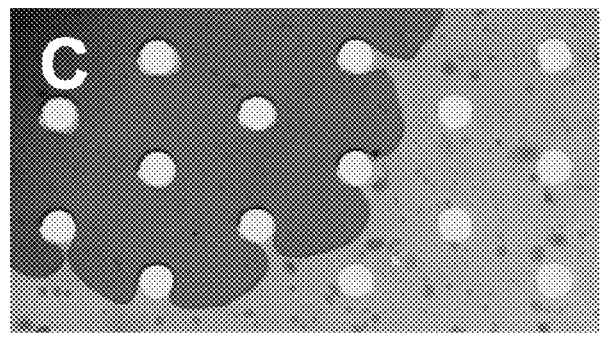
Figure 2D:
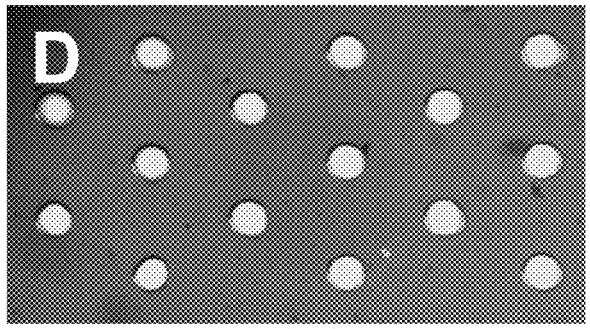

In one embodiment, the microchannel is primed with an immiscible fluid. Droplets are then formed by first flowing a fluid (such as aqueous solution) into the microchannel to fill the channel (see FIG. 2A). The wells remain coated with a thin film of the immiscible fluid. A second immiscible fluid (such as oil) is flowed into the channel (see FIGS. 2B and 2C). As the oil flows into the channel it displaces the water phase but leaves aqueous droplets in the wells (see FIG. 2D). These aqueous droplets are the same size of the wells. The oils used in this example are 1-octonal. The droplets are then released from the wells by flowing a release fluid through the channel, where the release fluid can include immiscible fluids such as hydrocarbon oils (mineral oil, 1-octanol and hexadecane) and perfluorinated oils (FC-40, Novec 7500). In another embodiment, the release of droplets is by an increase in flow speed of the immiscible fluid, where the flow rate is greater than 0.1 mm/sec. In other embodiments, the flow rates are shown in TABLE 1.

TABLE 1

| SOLUTION | FLOW RATE RANGE |
| --- | --- |
| Purge of Immiscible Fluid | 0.01 mm/sec to 500 mm/sec |
| Aqueous Fluid | 0.01 mm/sec to 500 mm/sec |
| Immiscible Fluid | 0.01 mm/sec to 500 mm/sec |
| Droplet Release Fluid | 1 mm/sec to 1000 mm/sec |

According to a further embodiment, the invention offers several advantages over conventional techniques. The size of droplets is defined by the size of the depressions and is therefore tunable and robust, where the depressions are formed using lithography. The position of the droplets is predefined and thus the position can be programmed in the detection setup. The formation of droplets is robust and relatively invariant to flow speeds of fluids. Furthermore, the reagents can be flowed through in line, one after the other, removing the need for multiple fluid control systems for aqueous reagents and oil in a device and simplifying the off-chip instrumentation. Moreover, the droplet array can be formed by injecting the fluids using a pipetman for facilitating its application with assays and eliminating the need for external fluid control.

The device shown in FIGS. 2A-2D is fabricated using soft lithography. In this example, the device is made of polydimethylsiloxane (PDMS) bonded permanently to a glass coverslide using a plasma cleaner. In a further embodiment, the surface of the microchannel is rendered superhydrophobic by treatment with 1720 Electronic Grade Coating (3M).

According to other embodiments, the process of droplet formation does not depend on device material and therefore suitable materials for the device would include, but not be limited to, glass, PDMS, plastics and polymers. The depth of the channel and well can be varied from 100 nm-1 mm. The width of the well can be varied from 100 nm-1 mm. Suitable average flow speeds for the fluids in the channel would span from 0.01 to 500 mm/sec. Aspect ratios of depth of channel to well can range 1:1.1 to 1:20. Aspect ratio of well diameter to minimum spacing between individual wells can range 20:1 to 1:10. The shape of the wells is variable (top view) and includes spherical, oval or square.

The requirement for the fluids is that they be immiscible. This also includes combinations of gas and liquids. Surfactants can be included in either the droplet or external fluid to lower interfacial tension and/or reduce surface wetting of the droplets.

Some variations include changing the configuration or shape of the wells could lead to droplets of different size or shape. The system can also be used to produce oil droplets in water. This system can also be used with a fluid/gas system to produce gas bubbles in liquid in predetermined positions. According to another aspect of the invention, the microchannel is treated with a hydrophobic coating, where the microwells comprise the hydrophobic coating. In a further aspect of the invention, the microchannel is treated with a hydrophilic coating, where the microwells comprise the hydrophilic coating.

The most prominent application for the current invention is digital Polymerase Chain Reaction PCR, where the invention offers a new and more robust device and method to prepare the droplets for the PCR analysis. It simplifies the requirements relating to fluid control with fluids brought in sequentially by a single entry and exit. The biological preparation (PCR cycles) are performed on-chip with simultaneous detection of the droplet array.

In one embodiment, the injection of fluids in the device can be performed using syringe and syringe pumps. However, since only a single entry point is needed, the solutions can be injected using a single syringe or a pipette.

The method can also be used to process an emulsion with variable droplet size to create an organized array or to produce homogeneous sized emulsion. The droplets can be ejected from the well array by a high flow rate of the external phase for further processing or collection off-chip.

The method can be used to make an array of gels at predetermined positions for cellular or protein assays. In this case, droplets containing gelling reagent (such as alginate or matrigel) would be prepared by the method according to the current invention at a temperature where the reagent remains fluid. After formation of the gel, the temperature is modified to the gelation temperature to provoke gelation. The external oil can be replaced with aqueous solutions such as buffers or media.

Other applications of the device are to arrange an array of polymer solutions using the method of the current invention, followed by polymerization in the array (by light, heat or chemical), if needed the beads can be ejected off chip by using a high flow of the external fluid.

The invention can also be used to make arrays of unilamellar vesicles or giant-unilamellar vesicles (GUVs). Lipid-stabilized aqueous droplets are produced by the method described. The external oil can then be replaced with an aqueous phase. When the droplets traverse the oil-lipid interface the lipid bilayer of the vesicle is formed. In this way, vesicle arrays of large size (hundreds or thousands of vesicles) can be made by microfabricating holes in the channel surfaces. Asymmetric vesicles can be obtained by switching the dissolved lipid content in the oil phase before introduction of the aqueous phase. Furthermore, multiple oil or water entries can be used to produce vesicles with variable and predictable lipid composition and content through the breadth of the array. After formation the GUVs (or lipid-stabilized aqueous droplets) can be ejected from the wells using a high flow rate of external fluid.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of forming microdroplets, comprising:
   a. forming a well plate, using lithography, wherein said well plate comprises a microchannel and a microwell in a surface of said microchannel;
   b. flowing a first fluid into said microchannel, wherein said microchannel and said microwell are filled with said first fluid; and
   c. flowing a second fluid into said microchannel, wherein said first fluid is displaced from said microchannel, wherein said first fluid remains in said microwell, wherein a microdroplet of said first fluid is formed;
   wherein an aspect ratio of a depth of said microchannel to a depth of said microwell is in a range of 1:1.1 to 1:20.

2. The method according to claim 1 further comprising priming said microchannel using said second fluid by flowing said second fluid into said microchannel to fill said microchannel prior to said flowing said first fluid into said microchannel, wherein said microwell is coated with a thin film of said second fluid.

3. The method according to claim 1, wherein said microwell comprises a shape selected from the group consisting of a cylinder, a rectangle, an oval and a hemisphere.

4. The method according to claim 3, wherein a diameter of said microwell is in a range of 0.1 μm to 0.5 cm.

5. The method according to claim 1, wherein said microchannel comprises a height in a range of 0.1 μm to 0.1 cm.

6. The method according to claim 1, wherein said microchannel comprises an array of said microwells.

7. The method according to claim 6, wherein an aspect ratio of a diameter of said microwell to a minimum spacing between each said microwells is in a range of 20:1 to 1:10.

8. The method according to claim 1, wherein said microchannel comprises a material selected from the group consisting of glass, PDMS, plastics and polymers.

9. The method according to claim 1, wherein said lithography comprises soft lithography.

10. The method according to claim 1 further comprises treating said microchannel with a hydrophobic coating, wherein said microwells comprise said hydrophobic coating.

11. The method according to claim 1 further comprises treating said microchannel with a hydrophilic coating, wherein said microwell comprises said hydrophilic coating.

12. The method according to claim 1, wherein flow speeds of said fluids in said microchannel are in a range of 0.01 to 500 mm/sec.

13. The method according to claim 1 further comprising adding a surfactant to said microdroplet or to said second fluid thereby reducing an interfacial tension and surface wetting of said microdroplet.

14. The method according to claim 1 further comprising ejecting said microdroplet from said microchannel using an external fluid at a flow rate greater than 0.1 mm/sec.

15. The method according to claim 14, wherein said external fluid is selected from the group consisting of FC-40, hexadecane, mineral oil, silicone oil and water.

16. The method according to claim 1, wherein said first fluid or said second fluid comprises a gelling reagent, wherein said flowing of said gelling reagent into said microchannel occurs at a liquid temperature for said gelling reagent.

17. The method according to claim 1, wherein said first fluid comprises a polymer solution, wherein the method further comprises polymerizing said polymer solution in said microwell using a polymerizer selected from the group consisting of light, temperature and chemical reaction.

18. The method according to claim 1, wherein said microdroplet comprises a lipid-stabilized aqueous microdroplet, wherein said second fluid comprises an aqueous liquid containing a second lipid that is used to interface said lipid-stabilized aqueous microdroplet, the method further comprising causing an oil-second lipid interface to traverse said microchannel and said lipid-stabilized aqueous microdroplet to form a lipid bilayer microdroplet, wherein said lipid bilayer microdroplet comprises an aqueous outer layer to form a giant-unilamellar vesicle.

19. The method according to claim 18 further comprising using a plurality of liquid entries connected to said microchannel, wherein said plurality of liquid entries are configured to produce a plurality of microdroplets with variable and predictable lipid-stabilized composition and content across an array of microwells of said microchannel.

20. The method according to claim 1, wherein said lithography comprises using an emulsion that forms microwells configured for forming variable microdroplet sizes or homogeneous microdroplet sizes in an organized array of microdroplets.

* * * * *